United States Patent [19]
Faulkner

[11] Patent Number: 5,749,826
[45] Date of Patent: May 12, 1998

[54] URINARY INCONTINENCE CONTROL DEVICE

[76] Inventor: James W. Faulkner, 20 Regent Wood, Northfield, Ill. 60093

[21] Appl. No.: 743,709

[22] Filed: Nov. 6, 1996

[51] Int. Cl.[6] ........................................ A61F 2/00
[52] U.S. Cl. .............. 600/29; 600/31; 128/DIG. 25; 604/280; 604/283
[58] Field of Search ................. 600/29–31; 128/772, 128/833, 834, 840, DIG. 25; 604/51, 54, 57, 280, 283, 256, 164, 167, 169, 170

[56] References Cited

U.S. PATENT DOCUMENTS

| | | | |
|---|---|---|---|
| 3,923,066 | 12/1975 | Francisoud et al. | 128/348 |
| 4,932,938 | 6/1990 | Goldberg et al. | 604/96 |
| 4,995,868 | 2/1991 | Brazier | 604/105 |
| 5,041,092 | 8/1991 | Barwick | 604/104 |
| 5,114,398 | 5/1992 | Trick et al. | 600/29 |
| 5,193,533 | 3/1993 | Body et al. | 128/207.14 |
| 5,234,409 | 8/1993 | Goldberg et al. | 604/96 |
| 5,306,226 | 4/1994 | Salama | 600/29 |
| 5,374,254 | 12/1994 | Buma | 604/175 |
| 5,391,152 | 2/1995 | Patterson | 604/280 |
| 5,454,790 | 10/1995 | Dubrul | 604/104 |
| 5,509,889 | 4/1996 | Kalb et al. | 600/30 |

OTHER PUBLICATIONS

Nielsen, et al., "The Urethral Plug: A New Treatment Modality For Genuine Urinary Stress Incontinence in Women", *The Journal of Urology*, (1990), 144, 1199–1202.
Nielsen, et al., "The Urethral Plug II: An Alternative Treatment in Women with Genuine Urinary Stress Incontinence", *British Journal of Urology*, (1993), 72, 428–432.

*Primary Examiner*—Jennifer Bahr
*Assistant Examiner*—Rosiland Kearney
*Attorney, Agent, or Firm*—Grace J. Fishel

[57] ABSTRACT

A urinary incontinence control device including a catheter with a laterally extending projection which can be elastically deformed by an actuator from a protruding position for retention to a non-protruding position for catheter insertion and removal. The actuator is slidably disposed in the catheter for retracting the projection. The catheter has a connector at a proximal end for locking the actuator in the catheter when the projection is retracted facilitating insertion and removal of the device in the urinary tract of a human female.

8 Claims, 2 Drawing Sheets

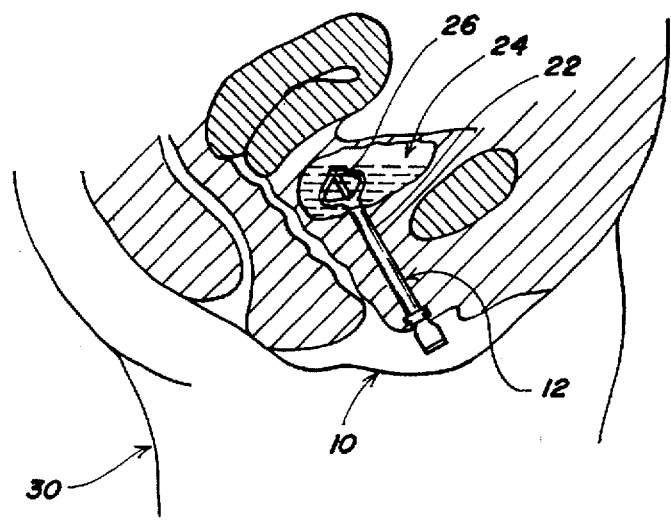
FIG. 1
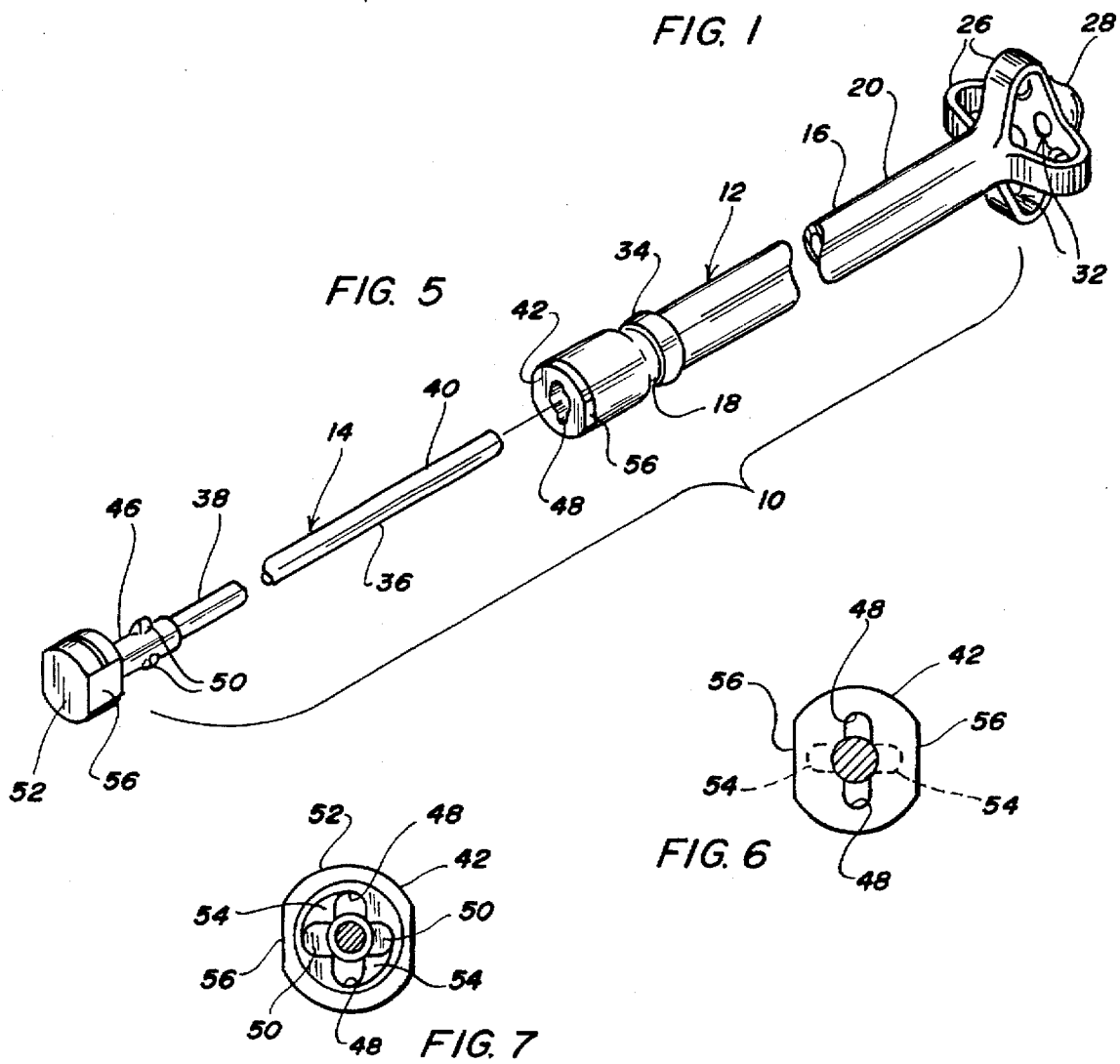
FIG. 5
FIG. 6
FIG. 7

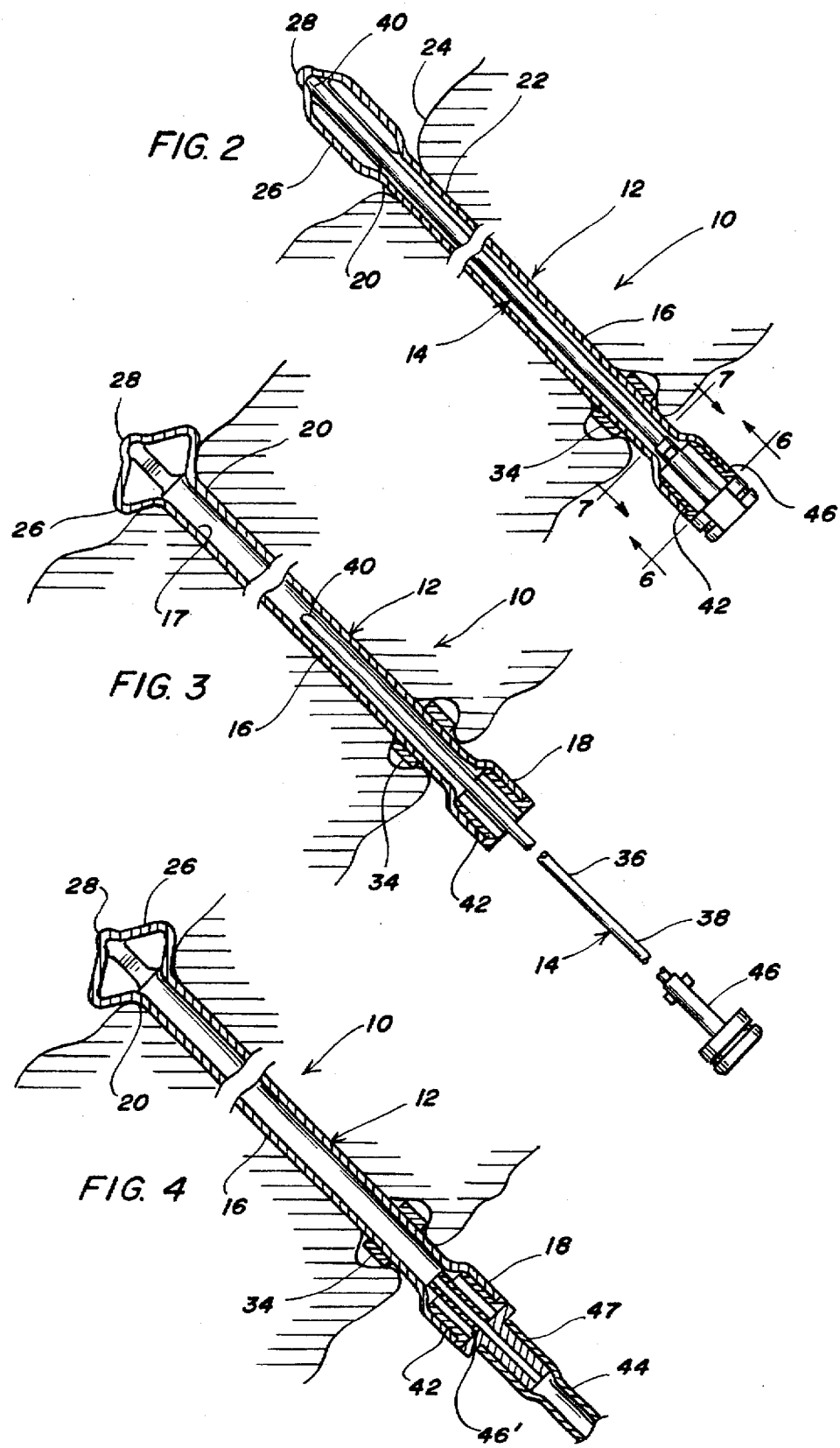

URINARY INCONTINENCE CONTROL DEVICE

BACKGROUND OF THE INVENTION

1. Field of the Invention

The present invention relates to a unitary structure for inserting and removing an indwelling catheter for the control of urinary incontinence.

2. Brief Description of the Prior Art

Urinary incontinence is an unfortunate fact for growing numbers of women, resulting from an ever increasing older population. Such incontinence runs the gamut from minor loss of urine from coughing or sneezing to total loss even at rest. Causative factors are numerous, including the loss of bladder support after pregnancies and the long-term effect of gravity, producing a descent of the bladder and a weakening of the urethral sphincter, resulting in varying degrees of stress incontinence. Neurogenic factors may totally unable the patient to initiate urination or may cause constant or intermittent leakage.

Some known methods for dealing with urinary incontinence include the perineal exercises of Kegel, anticholinergic drugs to reduce bladder tone, and various surgical procedures, such as the Marshall-Marchetti-Kranz urethral suspension and the less invasive procedures of Stamey, Raz and Gittes, as well as pubovaginal slings. Kegel exercises do not help many women and anticholinergic drugs are indicated only in special circumstances. Where applicable, however, these methods or surgery have helped many women, especially those who are otherwise capable.

There remain, however, many more patients who elect not to have surgery, or for whom surgery fails, or who, because of age, physical or mental inadequacies, are not considered good surgical candidates. Known methods for treating these women focus on drainage control and include catheters and absorbent pads, from panty liners to diapers. Catheters and absorbent pads are awkward to use, inhibit activities and are a potential source of embarrassment to the user. Wet pads emit a distasteful uriniferous odor and catheters are usually connected to an external fluid collection system. The external fluid collection system inhibits the user's activities and can provide a path for bacterial infection. Many women are seen in nursing homes, able to mobilize with their walkers, but dragging long drainage tubes and urinary collection bags.

For the patient who is obtunded or is otherwise not capable of taking care of themselves, catheters and adsorbent pads place an enormous burden on caretakers in nursing homes and heath care facilities, involving repeated diapering at considerable expense in materials and time and multiple linen changes with an every present threat of the formation of decubiti. The alternative, which is usually a Foley catheter with a drainage tube, requires significant care and limits the motion of the patient lest the drainage tube be inadvertently caught and the catheter pulled out.

It is to the problems of women using catheters or absorbent pads for drainage control that the present invention is addressed. There have been valved incontinence devices for insertion into a patient's urethra to eliminate the need for external collection systems such as bags and pads. Examples of such devices are shown in U.S. Pat. Nos. 4,553,959; 5,030,199; 5,114,398 and 5,306,226 but none of the prior art devices have found general acceptance. Most are too complicated to use (i.e., requiring skilled nursing help for insertion and removal, not always available in nursing homes and the like), too costly or are ineffective for their intended purpose.

SUMMARY OF THE INVENTION

In view of the above, it is an object of the present invention to provide a urinary incontinence control device, comprising a unitary structure for insertion and removal. It is another object to provide a device that ensures that the anchoring tip is in the required expanded state for retention in the body or contracted state for insertion and removal from the body, said structure providing readily discernable means for checking that the tip is in the required condition. Another object is to provide a catheter with a manually actuable control valve for controlling urinary discharge. Other objects and features of the invention will be in part apparent and in part pointed out hereinafter.

In accordance with the invention, a unitary structure for placement and removal of a urinary incontinence control device includes a catheter with a laterally extending projection which can be elastically deformed by an actuator from a protruding position for retention to a non-protruding position for catheter insertion and removal. The catheter has a hollow, flexible tube having a distal end and a proximal end and is adapted to be inserted into a urethra of a human female patient. The distal end of the catheter is outfitted with a laterally extending, retractable projection that is biased outwardly in the natural state and serves as a retention structure in the bladder of the patient. A semi-rigid actuator, with a distal end and a proximal end, is slidably disposed in the catheter. The distal end of the actuator is effective to retract the projection so that the catheter can pass through the urethra into the bladder, for placement and removal of the device. A connector is attached to the proximal end of the catheter in which a plug attached to the proximal end of the actuator is received and locked when the projection is retracted by the actuator.

The invention summarized above comprises the constructions hereinafter described, the scope of the invention being indicated by the subjoined claims.

BRIEF DESCRIPTION OF THE DRAWINGS

In the accompanying drawings, in which one of various possible embodiments of the invention is illustrated, corresponding reference characters refer to corresponding parts throughout the several views of the drawings in which:

FIG. 1 is a simplified schematic anatomical view showing a urinary incontinence control device in accordance with the present invention in the urinary tract of a human female patient during insertion or removal;

FIG. 2 is a side elevation in section showing the urinary incontinence control device as shown in FIG. 1;

FIG. 3 is a side elevation in section showing the urinary incontinence control device while a stylet is being removed or reinserted in a catheter with a Malecot tip;

FIG. 4 is a side elevation in section showing the urinary incontinence control device with a drainage tube attached;

FIG. 5 is an exploded perspective view of the urinary incontinence control device;

FIG. 6 is a view of a connector taken in the direction of line 6—6 in FIG. 2; and, FIG. 7 is a view of the connector taken in the direction of line 7—7 in FIG. 2.

DETAILED DESCRIPTION OF THE INVENTION

Referring to the drawings more particularly by reference character, reference numeral 10 refers to a urinary incontinence control device in accordance with the present invention. Device 10 in major part includes a catheter with a laterally extending projection which can be elastically deformed by an actuator 14 from the protruding position for retention to a non-protruding position for catheter insertion and removal. Catheter 12 is a hollow, flexible tube 16 formed of a biocompatable, medically acceptable elastic material such as latex, silicone rubber and the like. For long term placement, catheter 12 should be formed of a material having the ability to remain soft and flexible for long periods of time without body rejection or tissue reaction.

Tube 16, as shown in FIG. 3, has a proximal end 18 and a distal end 20. To prevent migration of tube 16 relative to a urethra 22, tube 16 has a first anchoring structure 26 larger than the diameter of the urethra in the neck portion of a bladder 24 and a second anchoring structure 34 at the external opening of the urethra. The anchoring structure in the bladder comprises a laterally extending projection, illustrated as a plurality of retractable, flexible flanges 26 which are formed at the distal end of tube 16. Tube 16 is adapted to be engaged by actuator 14, illustrated as a stylet, as more particularly described below and, in simplest form, terminates in a closed end 28. Flanges 26 are biased outwardly in their natural state and catheter 12 has an intrinsic length and diameter, when not under axial stress or radial compression, whereby flanges 26 are adapted to retain the catheter in bladder 24 and tube 16 is adapted to fit within and engage urethra 22 of a patient 30. A fluid drainage passage 17 extends through catheter 12 communicating proximal end 18 with gaps 32 between flanges 26. The anchoring structure at the external opening of the urethra is a soft rounded ring 34 that surrounds and is slidably mounted on tube 16.

Stylet 14 includes a semi-rigid rod 36 with a proximal end 38 and a distal end 40 and is slidably disposed in passage 17 of catheter 12. Stylet 14 has a length greater than catheter 12 with distal end 40 adapted to engage distal end 20 of tube 16. Axial movement of stylet in catheter 12 applies a desired axial stress to the catheter effective to retract the flanges 26. In the simplest case, the distal end of stylet 14 may be a blunt tip, where the blunt tip engages closed end 28. As stylet 14 retracts flanges, it also elongates tube 16, further facilitating insertion and removal of the catheter. Subsequent removal of the stylet 14 from the catheter, permits flanges 26 to reassume their outwardly biased form and engage bladder 24. Tube 16 likewise reassumes its normal diameter and is sealed against urethra 22.

A tubular connector 42 is attached to proximal end 18 of catheter 16, for latching proximal end 38 of stylet 14 and for connection of a drain tube 44, or the like. Connector 42 is adapted to depend on tube 16 from the external orifice of the urethra, preferably only a short distance, and, in some instances, may be concealed in the folds of the labia majora. Connector 42 has an internal passage 19 communicating with the fluid drainage passage 17 in tube 16 in which a plug 46 on proximal end 38 of stylet 14 is received and locked when flanges 26 are retracted. In the form illustrated, connector 42 is a sleeve with a pair of opposing internal axial grooves 48 and plug 46 has a pair of protruding pins 50 and a head 52. When plug 46 is inserted in sleeve 42, pins 50 are received and slide along axial grooves 48, each of which opens into a transverse slot 54, and underside of head 52 is stopped against a proximal end of the sleeve 42. Locking of plug 46 in connector 42 is accomplished by inserting tip of plug 46 causing pins 50 to slide along transverse slots 54 and turning of head 52 to lock. Transverse slots 54 are not interconnected so that plug 46 is stopped at less than half rotation, preferably at about a quarter of a turn. An alignment indicia, such as a flat or oval surface 56, can be provided on the outside of the sleeve and a corresponding flat or oval surface 56 can be provided on the outside of head 52, which indicia when aligned indicate that stylet 14 is locked in connector 42. In other instances, transverse slots 54 may be inclined with a recessed depression at the peak of the slanted surface serving as a detent for the pins. Arrival of stylet 14 at its required position is confirmed to the user by a slight snap action detected through plug 46 as pins 50 enter the detent.

In use, stylet 14 is inserted into catheter 12 and plug 46 locked in connector 42. In this condition, device 10 forms a unitary structure for insertion and removal of the catheter using only one hand. The exterior of catheter 12 may be coated with a lubricant and an antibiotic substance prior to insertion into urethra 22 and bladder 24 or, alteratively, such substances can be injected into the patient's urethra prior to insertion of device 10. As shown in FIG. 2, when flanges 26 are retracted, the reduced diameter of the distal tip of tube 16 is such that the outer diameter at the flanged distal end of the catheter is approximately equivalent to the outer diameter of the catheter tube. This reduced diameter minimizes the risk of damage to the urethra and bladder during insertion or withdrawal of the catheter.

After catheter 12 has been inserted an appropriate distance (e.g., from about 1¼ inch to about 1½ inch), stylet 14 is turned to unlock from sleeve 42 and removed as shown in FIG. 3, releasing the axial tension so that flanges 26 unfurl in bladder 24 and tube 16 expands and seals against the walls of the urethra. Ring 34 can then be slid against the meatus, completing the installation of the catheter. With continuing reference to FIG. 3, after stylet 14 is removed, rod 36 may be detached from plug 46 and plug 46 reinserted into connector 42 and locked into position with part of a turn, stopping the flow of urine and allowing the bladder to fill normally. Alternatively, a separate plug may be provided, if desired, and will be required, when rod 36 is not separable from plug 46.

After stylet 14 has been removed and while plug 46 is being inserted, if desirable to stop the flow of urine the operator can pinch tube 16 closed above connector 42 under finger pressure or with a clamp (not shown). After plug 46 installed, pressure on tube 16 is released. Plug 46 is palpable outside the orifice of the urethra and can be removed to permit user-controlled bladder drainage. When it is desired to start the flow of urine, tube 16 may be pinched closed and plug 46 removed. After the patient has finished voiding, plug 46 is reinstalled.

If it desired to permit continuous bladder drainage, as shown in FIG. 4, a drainage plug 46' with a drainage passage 47 is inserted and locked in connector 42. Tube 44 interconnects drainage plug 46' with a fluid collection member (not shown), permitting continuous drainage of fluid from the bladder.

Removal of catheter 12 from bladder 24 and urethra 22 is preceded by removal of plug 46 or 46' and insertion of stylet 14 in tube 16. With stylet 14 locked in connector 42, flanges 26 are automatically retracted and tube 16 stretched facilitating removal and obviating the possibility that device 10 will be inadvertently removed from the patient's body with flanges 26 in the protruded state. This feature of device 10 is very important as other incontinence devices require the person doing the insertion and removal of the catheter to be sufficiently familiar with the particular catheter to know what internal position is indicated by its relative external position and such skilled nursing help is not always available.

Concerns regarding infection with device 10 are no different than with Foley drainage and the patient can be placed on Trimethoprim 100 mg daily, or 50 mg Macrodantin daily, or the like, for further security, if needed.

From the above, it will be apparent that device 10 offers a number of advantages. For nursing home residents, it establishes good control, can eliminate continuous drainage apparatus attached to the bed-ridden, and allows the ambulatory to have much greater freedom while walking or with their walkers and wheelchairs. For the capable patient, device 10 allows for self-catheterization and self-operation without fear that leakage will occur. In such instances, the patient, freed from collection bags and pads, can go to work or social events, with assurance, draining their bladder at any time they wish and removing device 10 at any time they select.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A urinary incontinence control device for placement and removal in the urinary tract of a human female comprising:
   - a catheter having a distal end and a proximal end, said catheter adapted to be inserted into a urethra of a patient;
   - a laterally extending projection formed at the distal end of the catheter, said projection being biased outwardly in the natural state and adapted to retain the catheter in a bladder of a patient;
   - a semi-rigid actuator having a distal end and a proximal end, said actuator slidably disposed in said catheter and said distal end of the actuator effective to retract the projection, said retracted projection adapted to pass through a urethra into a bladder;
   - a connector is attached to the proximal end of the catheter within which the proximal end of the actuator is inserted and locked when the projection is retracted by the actuator, said actuator blocking the flow of urine through the connector,
   - a slidably adjustable anchoring structure at the proximal end of the catheter having a diameter larger than a urethra for preventing migration of the catheter at an external opening of a urethra,
   - whereby said catheter and actuator form a unitary structure facilitating insertion and removal of the catheter.

2. The device of claim 1 wherein the actuator is a stylet with a plug attached to the proximal end, said stylet received and locked in said connector through said plug.

3. A urinary incontinence control device for placement and removal in the urinary tract of a human female comprising:
   - a catheter having a distal end and a proximal end, said catheter adapted to be inserted into a urethra of a patient;
   - a plurality of retractable, flexible flanges formed at the distal end of the catheter, said flanges being biased outwardly in their natural state and adapted to retain the catheter in a bladder of a patient;
   - a semi-rigid stylet having a distal end and a proximal end attached to a plug, said stylet slidably disposed in said catheter and said distal end of the stylet effective to retract the flanges, said retracted flanges adapted to pass through a urethra into a bladder;
   - a connector is attached to the proximal end of the catheter within which the plug on the proximal end of the stylet is inserted and locked when the flanges are retracted by the stylet, said plug blocking the flow of urine through the connector,
   - a slidably adjustable anchoring structure at the proximal end of the catheter having a diameter larger than a urethra for preventing migration of the catheter at an external opening of a urethra,
   - whereby said catheter and stylet form a unitary structure facilitating insertion and removal of the catheter.

4. The device of claim 3 wherein the connector is a sleeve with an axial groove and the plug has a protrusion which is received in the groove, said axial groove opening to a transverse groove extending partway around the sleeve, locking of plug in connector being accomplished by rotating plug causing the protrusion to slide along the transverse groove.

5. The device of claim 3 wherein the stylet is detachable from the plug, said plug serving as a user-controlled bladder drainage valve after the stylet has been removed from the catheter.

6. The device of claim 3 wherein a second plug is provided for use as a user-controlled bladder drainage valve when received and locked in the connector after the stylet has been removed from the catheter.

7. The device of claim 3 wherein a drainage plug attached to a collection system is provided for use to permit continuous bladder drainage when received and locked in the connector after the stylet has been removed from the catheter.

8. The device of claim 3 wherein the proximal end of the catheter extends below an external opening of a urethra and the catheter is adapted to be pinched closed above the connector to stop the flow of urine after the stylet has been removed and while the plug is being installed or removed from the connector.

* * * * *